United States Patent [19]

Kimura et al.

[11] Patent Number: 4,845,554
[45] Date of Patent: Jul. 4, 1989

[54] AUTOMATIC LIGHT ADJUSTING SYSTEM FOR AN ENDOSCOPE USING AN EXTERNALLY FITTER CAMERA

[75] Inventors: Kenji Kimura, Tachikawa; Kenichi Kikuchi, Hachiohji, both of Japan

[73] Assignee: Olympus Optical Co., Ltd., Tokyo, Japan

[21] Appl. No.: 135,179

[22] Filed: Dec. 18, 1987

[30] Foreign Application Priority Data

Dec. 19, 1986 [JP] Japan .................................. 61-303287

[51] Int. Cl.⁴ .......................... H04N 7/18; H04N 5/30
[52] U.S. Cl. ..................................... 358/98; 358/211; 128/6
[58] Field of Search ......................... 358/98, 211, 228; 128/4, 6

[56] References Cited

U.S. PATENT DOCUMENTS

| | | | |
|---|---|---|---|
| 4,190,864 | 2/1980 | Dischert | 358/228 |
| 4,396,951 | 8/1983 | Tanaka | 358/228 |
| 4,423,436 | 12/1983 | Kimura | 358/98 |
| 4,433,675 | 2/1984 | Konoshima | 128/6 |
| 4,516,172 | 5/1985 | Mujata et al. | 358/228 |
| 4,622,584 | 11/1986 | Nagasaki et al. | 358/98 |
| 4,653,478 | 3/1987 | Nagasaki et al. | 358/98 |
| 4,685,451 | 8/1987 | Ando | 128/6 |
| 4,720,178 | 1/1988 | Nishioka | 128/4 |
| 4,722,000 | 1/1988 | Chatenevec | 358/98 |

FOREIGN PATENT DOCUMENTS

| | | |
|---|---|---|
| 3129356 | 10/1984 | Fed. Rep. of Germany . |
| 3118341 | 5/1985 | Fed. Rep. of Germany . |
| 3432393 | 6/1986 | Fed. Rep. of Germany . |
| 57-11113 | 12/1982 | Japan . |

Primary Examiner—James J. Groody
Assistant Examiner—John K. Peng
Attorney, Agent, or Firm—Armstrong, Nikaido, Marmelstein, Kubovcik & Murray

[57] ABSTRACT

In an optical endoscope having an image guide transmitting to the exit end surface an optical image formed by an objective optical system, a video signal of an imaging circuit built in an externally fitted camera is displayed by a displaying device so that, even in case the optical image range of the imaging surface is different, the displayed video signal may be of a proper brightness by a light adjusting element variably controlling the illuminating light amount fed to the optical endoscope on the basis of the output signals of a detector for detecting the optical image range on the imaging surface and a detector for detecting the level of the video signal.

7 Claims, 6 Drawing Sheets

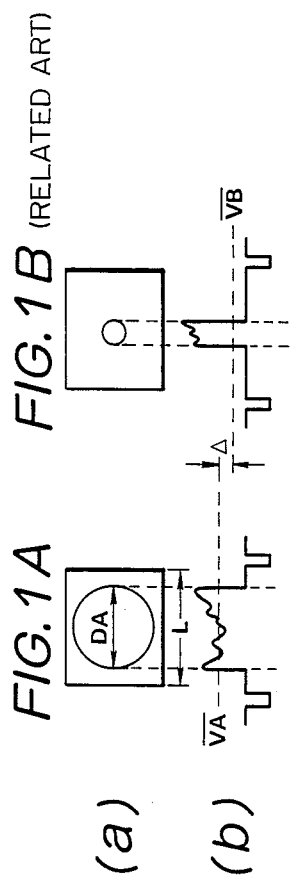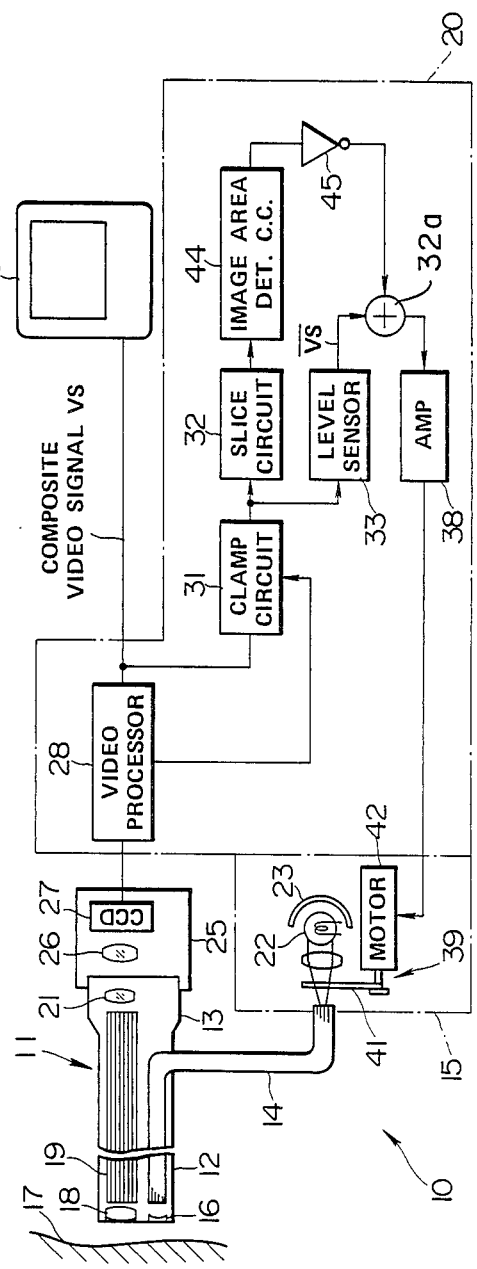

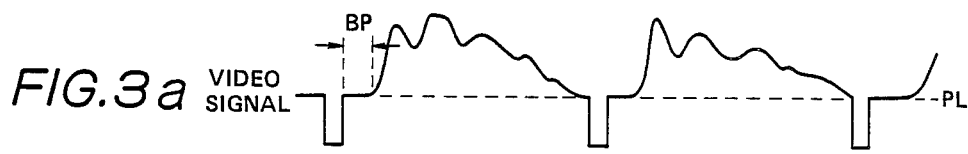
FIG.3a VIDEO SIGNAL
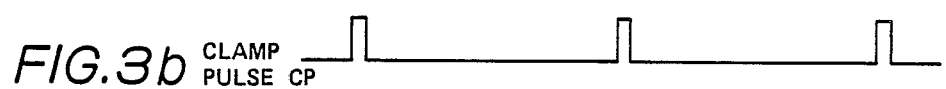
FIG.3b CLAMP PULSE CP
FIG.4
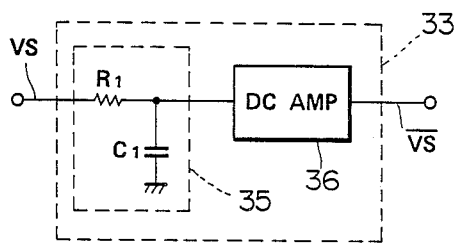
FIG.5
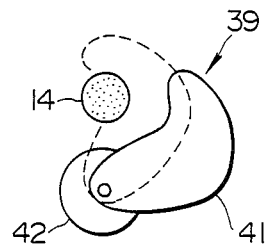
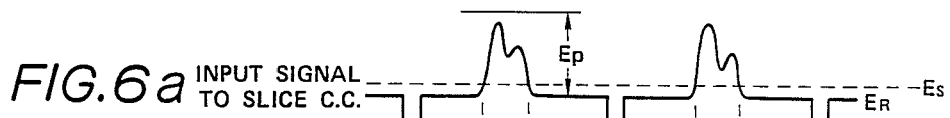
FIG.6a INPUT SIGNAL TO SLICE C.C.
FIG.6b OUTPUT SIGNAL OF SLICE C.C.

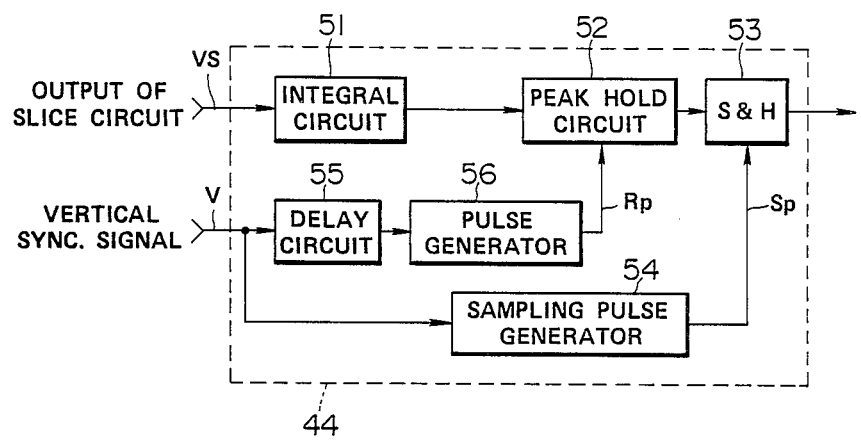
FIG. 7
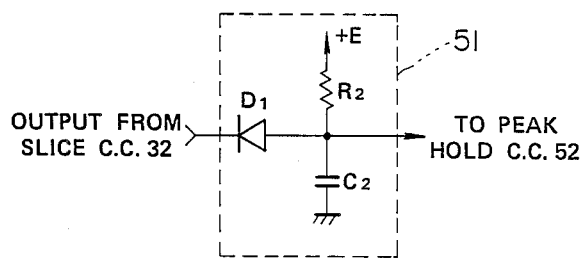
FIG. 8
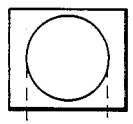
FIG. 9A    FIG. 9B
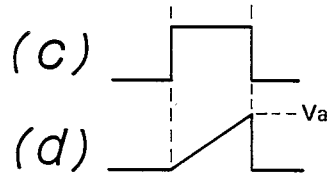

FIG. 10
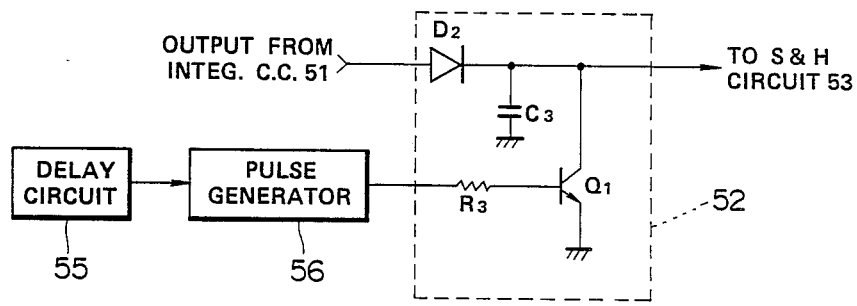
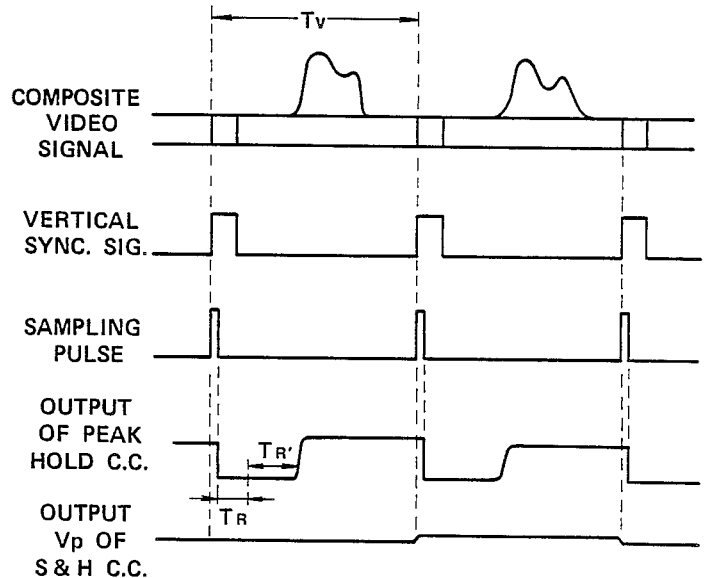
FIG. 11a  COMPOSITE VIDEO SIGNAL
FIG. 11b  VERTICAL SYNC. SIG.
FIG. 11c  SAMPLING PULSE
FIG. 11d  OUTPUT OF PEAK HOLD C.C.
FIG. 11e  OUTPUT $V_p$ OF S & H C.C.

AUTOMATIC LIGHT ADJUSTING SYSTEM FOR AN ENDOSCOPE USING AN EXTERNALLY FITTER CAMERA

BACKGROUND OF THE INVENTION

Field of the Invention and Related Art Statement

This invention relates to an automatic light adjusting system for an endoscope using an externally fitted camera wherein, even in case the image forming area varies, a proper light amount controlling function will be obtained.

Recently, there has come to be extensively used an endoscope (fiberscope) whereby an affected part or the like within a body cavity can be observed or treated to be cured by using a treating tool as required by inserting an elongated insertable part into the body cavity without requiring an incision.

In the observation or diagnosis with the above mentioned endoscope, in order to know whether the disease has recovered or not, it is necessary to record the state. In such case, often an externally fitted camera using such solid state imaging device as a CCD (charge coupled device) for the imaging means is fitted so that an optical image by a fiberscope may be converted to an electric video signal to be recorded by a VTR or the like or a photographic camera is fitted to take a photograph.

In some fiberscopes, the objective optical system is formed of a zooming optical system so that the magnification in the observation may be varied.

In the above mentioned zooming optical system, if the magnification is varied, the light amount will vary on the observed surface or photographed surface and will become unfavorable to recording or photographing.

Therefore, the present applicant has suggested in the patent gazette of Japanese patent laid open No. 211113/1982 an endoscope apparatus wherein the light amount is adjusted as operatively connected with the magnification variation of a zooming optical system to keep constant the incident light amount on the observed surface or photographed surface so that photographing or the like may be made with a proper exposure amount by utilizing this incident light amount.

This related art example is of a mechanism in which the light amount must be controlled as operatively connected with a zooming optical system. It is necessary to provide each fiberscope with this mechanism.

Now, in some case, it is desired to fit an externally fitted camera to not only a fiberscope of a zooming optical system but also a fiberscope of no zooming optical system so that a video image displayed in a monitor may be recorded by a VTR or the like.

In such case, there are various fiberscopes of image guide fiber bundles of large and small outside diameters in response to the uses.

For example, in FIG. 1A, (a) shows an optical image range DA of a fiber bundle within an imaging range L in case an externally fitted camera is fitted to a fiber scope having a large diameter image guide and (b) shows the video signal in such case.

On the other hand, with a fiberscope having a small diameter image guide, in the same manner, they are as shown in FIG. 1B.

In the case of fitting the above mentioned externally fitted camera, there is a prior art example wherein the illuminating light amount is adjusted to be on a proper level by an average value level, of a video signal. However, as shown in the above mentioned FIGS. 1A and 1B, the optical image range (picture image range of image area) formed on the imaging surface of the camera varies with the diameter of the image guide of the fiber scope and therefore the average value levels of the image signals fluctuate respectively as in VA and VB.

That is to say, in FIG. 1A, even if the rate of the range of the video image or picture image part to the range of the effective imaging range in the lateral direction is large and the amplitude of the video signal itself is small, the average level VA of the video signal will be large but, in FIG. 1B, unless the amplitude of the video signal itself is large, the average level VB of the video signal will become small. That is to say, due to the size of the image area, for example, a level difference Δ will be produced between them.

Therefore, even if an automatic light adjusting function automatically adjusting the illuminating light amount by the average level of a video signal is provided, in the method of the prior art example, if it is used for a fiberscope or the like different in the diameter of the image guide, the average level will also vary depending on the diameter and the illuminating light amount has not been able to be adjusted to a proper value. Therefore, the contrast of the picture image displayed on the monitor picture surface will be too bright or too dark. In the case of diagnosing with a monitor picture image, it will be likely to be difficult to well discriminate the affected part or the like.

Objects and Summary of the Invention

An object of the present invention is to provide an automatic light adjusting system for an endoscope using an externally fitted camera wherein, even in case the effective area of the image guide is different, the illuminating light can be automatically adjusted to a proper illuminating light amount.

Another object of the present invention is to provide an automatic light adjusting system for an endoscope having an externally fitted camera wherein, even in case the effective area of the image guide is different, an object image can be displayed automatically by a displaying means with a brightness making observation easy.

In the present invention, a means for detecting the level of a video signal output from a solid state imaging device and a means for detecting the image range of the video signal are provided and an automatic light adjusting means controlling the illuminating light amount fed to an optical endoscope by the output signals of these detecting means is formed so as to automatically adjust the light without depending on the effective area of the image guide.

BRIEF DESCRIPTION OF THE DRAWINGS

FIG. 1 is an explanatory view showing that the average value level of a video signal varies with the size of a picture image range on an imaging surface.

FIGS. 2 to 11 relate to the first embodiment of the present invention.

FIG. 2 is a formation diagram showing all of the first embodiment.

FIG. 3 is a waveform diagram showing a video signal output out of a video processor.

FIG. 4 is a circuit diagram showing the formation of a level sensor.

FIG. 5 is an explanatory view showing the formation of a light amount controlling part.

FIG. 6 shows waveform diagrams showing input and output signal waveforms of a slicing circuit.

FIG. 7 is a block diagram showing the formation of an image area detecting circuit.

FIG. 8 is a circuit diagram showing the formation of an integrating circuit.

FIG. 9 shows operation explaining diagram of an integrating circuit.

FIG. 10 is a circuit diagram showing the formation of a pulse generator.

FIG. 11 shows operation explaining waveform diagrams of a peak holding circuit and sample holding circuit.

DETAILED DESCRIPTION OF PREFERRED EMBODIMENT

Figure 12:
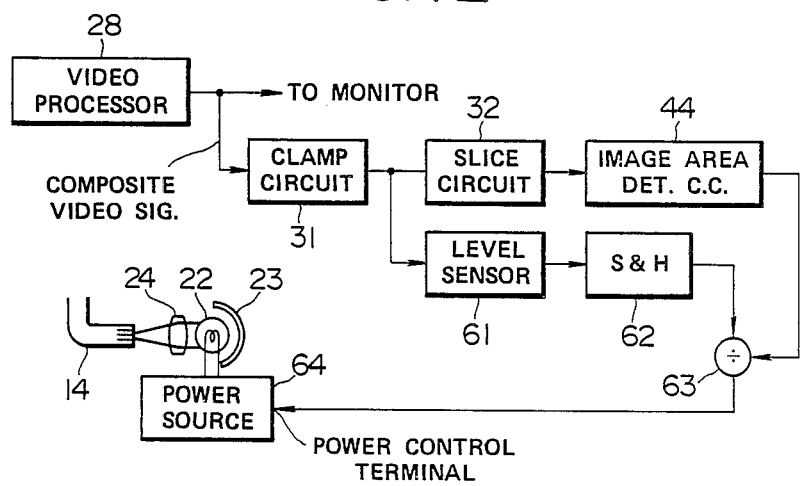
FIG. 12 is a formation diagram showing an essential part of the second embodiment of the present invention.

As shown in FIG. 2, reference numeral 10 includes a fiberscope 11 as an optical endoscope, an imaging camera 25 fitted to an eyepiece part 13 of this fiberscope 11, a light source apparatus 15 feeding an illuminating light to the entrance end surface of a light guide 14 of the above mentioned fiberscope 11, a signal processing part 20 processing a video signal output from the above mentioned camera 25 and a monitor 29 displaying an object image from an image signal of a predetermined system output from this signal processing part.

The above mentioned signal processing part 20 has a means for producing a light amount controlling signal for controlling the light amount of the illuminating light fed to the above mentioned light guide 14 from the above mentioned light source apparatus.

The above mentioned fiberscope 11 has an insertable part 12 elongated so as to be insertable into a body cavity and an eyepiece part 13 formed at the rear end of this insertable part 12. The illuminating light transmitting light guide 14 inserted through the insertable part 12 is extended out near the eyepiece part 13 and can be fitted at the entrance end to the light source apparatus 15 so that the illuminating light may be transmitted through this light guide 14 and may illuminate the object 17 side through a light distributing lens 16 from the tip surface.

An objective lens 18 is arranged in the tip part of the above mentioned insertable part 12. An image guide 19 formed of a fiber bundle is arranged on the front end surface (entrance end surface) in the focal plane of this objective lens 18 so that the formed image may be transmitted to the exit end surface on the eyepiece 13 side through this image guide 19 inserted through the insertable part 12 and may be observed by the naked eye from the rear of the eyepiece lens 21.

A light source lamp 22 is contained within the above mentioned light source apparatus 15. The illuminating light of this light source lamp 22 is reflected by a reflector 23, is condensed by a condenser 24 and is radiated onto the end surface of the light guide.

Now, the externally fitted camera 25 forming the first embodiment can be removably fitted to the above mentioned eyepiece part 13 and contains an imaging lens 26 and a CCD 27 as a solid state imaging device arranged in the focal plane of this imaging lens 26. An optical image transmitted to the eyepiece side through the image guide 19 is formed on the imaging surface of the CCD 27 by this imaging lens 26. The optical image formed on the imaging surface of this CCD is photoelectrically converted by this CCD 27, is then input into a video processor 28 through a transmitting cable, is processed to be converted to a composite video signal VS of such predetermined system as an NTSC system and is color-displayed by a monitor 29.

The above mentioned composite video signal VS shown in FIG. 3a is input into a clamping circuit 31 and is clamped in the direct current in a pedestal part corresponding to a black level by a clamping pulse CP shown in FIG. 3b. That is to say, the clamping pulse CP coincides substantially with the central position of the back porch range BP in the composite video signal VS. The pedestal PL is reproduced in the direct current as the 0 level by this clamping pulse CP. The composite video signal VS reproduced in the direct current in this pedestal PL is input into a slicing circuit 32 and level sensor 33 in the next step.

The above mentioned level sensor 33 is to detect the average value or peak value of the composite video signal VS and detects the average value in this first embodiment. FIG. 4 shows a concrete formation of this level sensor 33.

The composite video signal VS is input into an integrating circuit 35 formed of a resistance R1 and condenser C1. The average potential of the video signal VS detected by being integrated for 1 field period or 1 frame period by this condenser C1 is input into a direct current amplifier 36 to be amplified in the direct current and an average voltage signal VS of the video signal VS is output. By the way, the electric charge of the condenser C1 is reset in the vertical synchronous signal period or the like after the 1 field period or 1 frame period (not illustrated). The output of this level sensor 33 is amplified by an amplifier 38 through a mixer 37 and is input into a light amount controlling part 39 controlling the input light amount (radiated light amount) to the light guide 14. This comprises a light amount controlling member 41 and a driving motor 42 controlling the rotation amount of this light amount controlling member 41.

FIG. 5 shows an embodiment of the above mentioned light amount controlling part 39.

The normally and reversely rotatable motor 42 is fitted on its rotary shaft with a light amount controlling member 41 to be a diaphragm so that, when this motor 42 is normally rotated, the light amount controlling member 41 located in the position indicated by the solid line as retreated from the light path opposed to the end surface of the light guide 14 will rotate and move to the position indicated by the dotted line, will intercept a part of the light amount radiated onto the light guide 14 and will be able to variably control the light amount entering the light guide 14.

Now, the first embodiment is characterized in that a slicing circuit 32 slicing the part of a potential somewhat higher than the clamping potential of the video signal VS clamping in the direct current the output of the above mentioned clamping circuit, a image area detecting circuit 44 detecting the image area from the output of this slicing circuit 32 and a mixer 32a mixing the output of this image are detecting circuit 44 with the output of the level sensor 33 are provided to form a means for compensating the dependency on the image area in the light amount controlling signal.

The above mentioned slicing circuit 32 operates as shown in FIG. 6.

As shown in FIG. 6a, the video signal VS input into the slicing circuit 32 is clamped by a direct current potential $E_R$ on its pedestal level PL. The threshold value level (threshold potential) $E_s$ slicing in the slicing circuit 32 is set at a somewhat higher potential. This threshold value $E_s$ is set, for example, at a potential about 1/10 the saturated potential $E_p$ of the video signal VS. When passed through the slicing circuit 32 set at this slicing level, the video signal VS of the waveform in FIG. 6a will be of such waveform as is shown in FIG. 6b. That is to say, when the level of the input video signal VS exceeds the threshold value Es, the two-value signal switched from the "0" level to the "1" level will become the output signal of the slicing circuit 32.

As explained in FIG. 1, depending on the outside diameter and zooming rate of the fiberscope to be used, the range of the video signal will vary as shown in FIG. 9a and 9b. However, the object of this slicing circuit 32 is to detect this video signal range (or image range). the output of this slicing circuit 32 is input into the image area detecting circuit 44 in the next step and the image area of the actually obtained video signal is detected. FIG. 7 shows an embodiment of the image area detecting circuit 44.

The output of the slicing circuit 32 is input into an integrating circuit 51 and is integrated on the "1" level of the output signal of the slicing circuit 32. The output of this integrating circuit 51 is input into a peak holding circuit 52 and the peak value in the output signal of the integrating circuit 51 is detected, is input into a sample holding circuit 53, is sample-held by a sampling pulse $S_p$ of a sampling pulse generating circuit 54 becomes an output signal of this circuit 44. By the way, the vertical synchronous signal V is input into the sampling pulse generating circuit 54 to produce a sampling pulse $S_p$ and is input also into a pulse generator 56 through a delaying circuit 55 to produce a resetting pulse $R_p$ resetting a peak holding circuit 52 by the delayed vertical synchronous signal. This resetting pulse $R_p$ is to reset the peak holding circuit 52 just after the value peak-held by the peak holding circuit 52 is sample-held by the sampling pulse $S_p$.

An embodiment of the above mentioned integral circuit 51 is shown in FIG. 8. The output of the slicing circuit 32 is applied to one end of a condenser C2 through a reverse direction. This condenser C2 is earthed at the other end. Also, this condenser C2 is connected at one end to a positive current source end +4 through a resistance R2.

The operation of this integrating circuit 51 is as shown in FIG. 9.

FIG. 9A shows, for example, the case of a wide angle or a large diameter of the image guide. FIG. 9B shows the case of a wide angle or a large diameter of the image guide. In each of FIGS. 9A and 9B, the video image displayed on the picture surface of the monitor 29 is shown in (a), the video signal corresponding to this video image is shown in (b), the output waveform passed through the slicing circuit 32 is shown in (c) and the output of the above mentioned integrating circuit 51 is shown in (d).

The width (signal period) of the above mentioned video signal is different depending on the size of the image area and therefore the output pulse of the slicing circuit 32 also varies as shown in (c). The pulse shown in (c) is integrated by the integrating circuit 51 during that period to be of a saw tooth-like wave shown in (d).

In the above mentioned integrating circuit 51, in case the pulse shown in (c) in FIGS. 9A and 9B is "0", by the diode D1, the electric charge accumulated in the condenser C2 will be discharged and the potential of the condenser C2 will be reset but, on the other hand, in the case of the "1" level, the diode D1 will be cut off, the terminal voltage of the condenser C2 will rise toward a voltage +E with the resistance value of the resistance R2 and the capacity of the condenser C2 as time constants and, as a result, a saw tooth-like integrated wave of the waveform shown in (d) in FIGS. 9A and 9B will be obtained. This saw tooth-like integrated signal will be proportional to the pulse width in (c) or, in other words, the size of the image area.

The output of the above mentioned integrating circuit 51 is input into the peak holding circuit 52 to detect the peak value of the integrated signal.

An example of this peak holding circuit 52 is shown in FIG. 10. The output signal of the integrating circuit 51 is applied through a diode D2 to one end of a condenser C3 earthed at the other end to charge the condenser C3 and to hold the maximum potential (shown by Va and Vb in (d) in FIGS. 9A and 9B) of the integrated signal 9 shown in (d) in FIGS. 9A and 9B) integrated by the integrating circuit 51. The maximum potential held by this condenser C3 is input into a sample holding circuit 53 in the next step and is sample-held.

Now, as the level of the video signal fluctuates with the imaged object, the voltage peak-held at a time point will not always hold the maximum voltage after that time point. Therefore, in this first embodiment, a voltage held as charged by the condenser C3 by each field is reset. That is to say, a vertical synchronous signal V is input into a pulse generator 56 through a delaying circuit 55 to produce a resetting pulse $R_p$ just after a sampling pulse $S_p$. This resetting pulse $R_p$ is applied to the base of a transistor Q1 through a resistance R3 and the collector and emitter Of the transistor Q1 are switched on at this time to discharge and reset the condenser C3 to which this collector is connected.

FIG. 11 shows operating waveforms of the peak holding circuit 52 and sample holding circuit 53.

FIG. 11a shows a video signal by the scale of a vertical period $T_v$ and FIG. 11b shows a vertical synchronous signal V.

As shown in FIG. 11c, the sampling pulse $S_p$ is produced by a sampling pulse generating circuit 54 triggered, for example, on the front edge, that is, the rising edge of the vertical synchronous signal V. Therefore, with a pulse of a narrow width becoming "1" for a short period from the rising of this vertical synchronous signal V, the pulse period of this sampling pulse $S_p$ becomes a sampling period, the output of the peak holding circuit 52 is sample-held and is then immediately reset by the resetting pulse $R_p$ slightly delayed by the delaying circuit 55. In this case, the resetting pulse $R_p$ of the pulse generator 56 can be produced, for example, as the vertical synchronous signal V delayed by the delaying circuit 55. Then, the symbol $T_R$ in FIG. 11d will represent a resetting period. After the resetting by this resetting pulse $R_p$, until a video signal is generated, the period of the reset voltage will be $T'_R$. It is a role of the sample holding circuit 53 to replace the range of this period $T'_R$ with the peak-held voltage. It is possible to substantially perfectly obtain a direct current voltage $V_D$ as shown in FIG. 11e by sample-holding the peak-held voltage just before being reset. This voltage $V_D$ is a direct current signal corresponding to the size of the image area and is a direct current signal of a potential proportional to the size of the image area in this embodiment.

The output of the above mentioned sample holding circuit 53 is inverted through an inverter 45, is then mixed with the output of the level sensor 33 by the mixer 37 and is input into the motor 42 as a light amount controlling signal through the amplifier 38, that is to say, an offset voltage is added to the light amount controlling signal by the level sensor 33 so as to be a light amount controlling signal. In a controlling system in which the average voltage of a video signal is simply detected by the level sensor 33 and the light is adjusted and controlled with this detected signal to hold the light amount an a constant level, even if the average level of the video signal within the image area does not vary but only the image area becomes smaller, the voltage detected on the average value level of the video signal will be small and, as a result, there will be made an unfavorable light amount control in which the radiated light amount to the light guide by the light source will increase and the level of the video signal will be made high. On the contrary, if the image area is larger, the video signal level will be reduced. However, in this embodiment, a light amount controlling signal eliminating the variation of the video signal level in response to the image area variation is produced and is mixed by the mixer 37 so as not to be influenced by the image area variation.

That is to say, in case the image area varies from a reference image area and the output level of the level sensor 33 varies, the variation amount will be produced by an image area variation compensating (light amount controlling) signal producing means and will be inverted and mixed by the inverter 45 so that the level of the light amount controlling signal may not be varied by the component purely by the image area variation.

Therefore, according to this first embodiment, in case the externally fitted camera 25 is fitted to the fiberscope 11 and the video image of the imaged object 17 is displayed by the monitor 29, even in case the outside diameter of the image guide 19 is different and therefore the area of the picture image displayed on the picture surface of the monitor 29 is different, as the means for eliminating the dependency on the image area in the light amount controlling signal is formed, the illuminating light amount can be automatically adjusted always easily visibly.

In case the imaging lens 26 of the externally fitted camera 25 or the objective 18 of the fiber scope 11 is formed of a zooming optical system, even in case the zooming optical system is adjusted to vary the image area, the light amount controlling function will not mis-operate depending on the image area variation and the light can be automatically adjusted to be always in a preferable illuminating light amount state.

FIG. 12 shows an essential part in the second embodiment of the present invention.

As shown in FIG. 12, the output of the clamping circuit 31 in FIG. 2 is input into an integrating circuit 61 and is integrated and then the peak value of the integrated value is held by a sample holding circuit 62. This sample holding value is divided by the output signal of an image area detecting circuit 44 in a divider 63, the video signal is divided by the image area period T to detect the average level of the video signal in the image area period T and this signal is made a light amount controlling signal. That is to say, the average level of the video signal is regulated by the size of the image area to produce a light amount controlling signal not depending on the image area.

By the way, as in the first embodiment, the rotation of the motor 42 may be controlled by this light amount controlling signal to control the light amount passed by the light amount controlling member 41. However, in this embodiment, the light amount controlling signal is applied to an electric power controlling terminal of a power source 64 feeding an illuminating electric power to the lamp 22 to directly control the emitted light amount.

Figure 13:
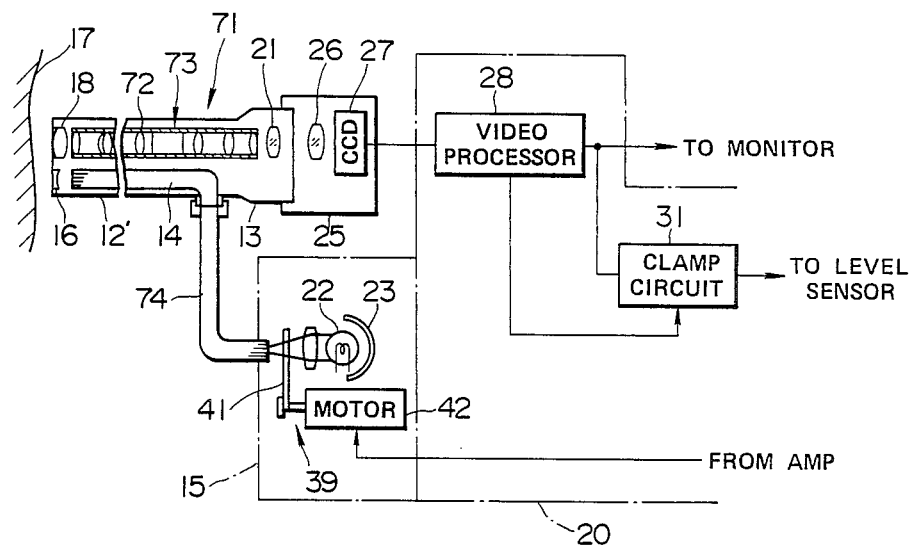
FIG. 13 is a formation diagram showing an essential part of a system of the third embodiment of the present invention.

FIG. 13 shows a part of a system in which a rigid endoscope 71 is used instead of the fiberscope 11 in the first embodiment.

In this rigid endoscope 71, the image guide 19 of the fiberscope 11 in FIG. 1 is formed of a relay optical system 73 arranged within an optical system containing pipe 72 and an insertable part 12' is formed of a rigid member.

By the way, the light guide 14 inserted through the insertable part 12' is connected with a light guide cable 73 near the eyepiece part 13 so that an illuminating light may be fed to the light guide 14 through this light guide cable 74. The others are of the same formation as of the fiberscope 11. This system has the same function as of the first embodiment.

Figure 14:
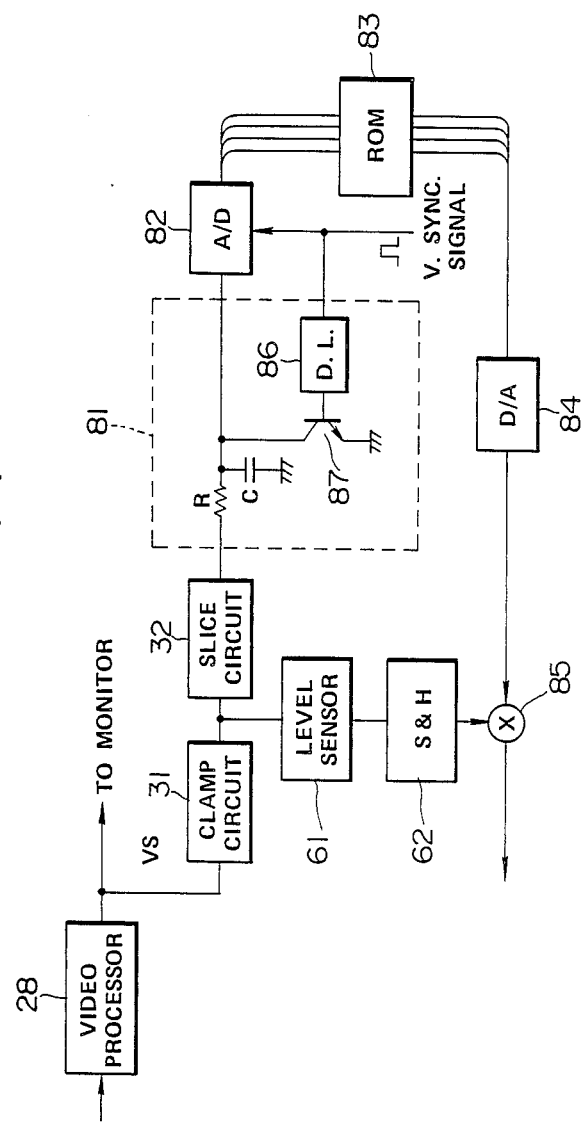
FIG. 14 is a formation diagram showing an essential part of the fourth embodiment of the present invention.

FIG. 14 shows an essential part of the fourth embodiment of the present invention.

In this embodiment, the output of the slicing circuit 32 is input into an image area detecting integrating circuit 81 and the signal integrated by this integrating circuit 71 is converted to a digital signal by an A/D converter 82. The output signal of this A/D converter 82 is applied to the address of a ROM 83, data written in advance are read out and are converted to an analogue signal by a D/A converter 84 and this analogue signal is multiplied by the output signal of a level sensor 61 through a sample holding circuit 62 to produce a light amount controlling signal.

The above mentioned integrating circuit 81 is formed of a resistance R and condenser C. The electric charge accumulated in the condenser C is reset, for example, by applying a vertical synchronous signal after 1 field/-frame period to the base of a switching transistor 87 through a delaying line 86. By the way, this vertical synchronous signal is applied to the A/D converter 82 as an A/D converted clock just before the electric charge of the condenser C is discharged, the maximum value voltage accumulated in the condenser C is A/D converted and the memory data of the ROM 84 are read out with the maximum value. By the way, when the A/D converter 82 of a type holding the A/D converted value on the "L" level is used, the A/D converted output will be held for a field/frame period.

In the above mentioned ROM 83, the larger the address value, the smaller the output data. Therefore, a light amount controlling signal not depending on the image area can be produced when multiplied with the multiplier 85.

In the above mentioned fourth embodiment, the A/D converter 82 and D/A converter 84 of a comparatively low speed can be used. By the way, a circuit sample-holding the output of the integrating circuit 81 may be interposed.

By the way, the present invention can be applied to an optical endoscope having a zooming optical system and can use also a camera having a zooming optical system.

What is claimed is:

1. An automatic light adjusting system for an endoscope using an externally fitted camera, comprising;

an optical endoscope having an image forming objective optical system arranged on the tip side of an elongated insertable part, an image guide inserted through said insertable part and transmitting to the exit end surface an optical image formed on the entrance end surface by said objective optical system and a light guide inserted through said insertable part and transmitting and emitting from the exit end surface an illuminating light;

an externally fitted imaging camera fittable to an eyepiece part containing said exit end of said image guide and containing an imaging means comprising an imaging optical system and a solid state imaging device arranged so as to have its imaging surface located in the focal plane of said imaging optical system;

a light source means feeding an illuminating light to the entrance end surface of said light guide of said optical endoscope;

a video signal processing means for receiving a video signal output from said solid state imaging device and producing a predetermined video signal;

a displaying means for displaying on a displaying picture surface the predetermined video signal output from the video signal processing means;

a clamping means for clamping said predetermined video signal received from said video signal processing means;

a video signal level detecting means receiving the output of said clamping means for detecting the video signal level on the basis of the output form said solid state imaging output of said clamping means;

an image range detecting means for receiving the output of said clamping means, for detecting the image signal level in the whole image range, and for outputting an image range corresponding signal corresponding to the image range formed on the imaging surface of said solid state imaging device; and a light amount controlling means for controlling the illuminating light amount fed from said light source means to said light guide with a light amount controlling signal made by mixing said video signal level and said image range corresponding signal with each other.

2. A system according to claim 1 wherein said video signal detecting means is formed of a direct current reproducing circuit extracting the pedestal of a composite video signal output from said video signal processing means and an integrating circuit integrating for 1 field/frame period displayed by interlace/non-interlace scan an output signal of said direct current reproducing circuit having this pedestal on the 0 level.

3. A system according to claim 1 or 2 wherein said image range detecting means is formed of a slicing circuit slicing on a reference level the predetermined video signal output from said video signal processing means, an integrating circuit integrating the output signal of said slicing circuit for 1 field/frame period, a sample-holding means sample-holding the output signal of said integrating circuit after 1 field/frame period and a resetting circuit resetting the output signal of said integrating circuit after said sample holding.

4. A system according to any of claims 1 and 2 wherein said light amount controlling means is formed of a diaphragm varying the passed light amount of an illuminating lamp fed to said light guide in response to the rotation angle around a rotary shaft and a motor having said diaphragm fitted to a rotary shaft and having its rotation angle controlled by said light amount controlling signal.

5. A system according to any of claims 1 and 2 wherein said light amount controlling means has said light amount controlling signal applied to a terminal controlling the output electric power of an electric power source circuit feeding an electric power to a lamp feeding an illuminating light to said light guide.

6. A system according to any of claims 1 and 2 wherein said optical endoscope is a fiberscope wherein said image guide is formed of a flexible fiber bundle.

7. A system according to any of claims 1 and 2 wherein said optical endoscope is a rigid endoscope wherein said image guide is formed of a relay optical system.

* * * * *